(12) United States Patent
Uchida et al.

(10) Patent No.: US 7,110,112 B2
(45) Date of Patent: Sep. 19, 2006

(54) CONCENTRATION MEASURING INSTRUMENT, CONCENTRATION MEASURING CONTACT APPARATUS, CONCENTRATION MEASURING CALCULATING APPARATUS, AND CONCENTRATION MEASURING METHOD

(75) Inventors: Shinji Uchida, Osaka (JP); Masahiko Shioi, Osaka (JP)

(73) Assignee: Matsushita Electric Industrial Co., Ltd., Osaka (JP)

( * ) Notice: Subject to any disclaimer, the term of this patent is extended or adjusted under 35 U.S.C. 154(b) by 327 days.

(21) Appl. No.: 10/479,758

(22) PCT Filed: Mar. 5, 2003

(86) PCT No.: PCT/JP03/02534

§ 371 (c)(1),
(2), (4) Date: Jun. 10, 2004

(87) PCT Pub. No.: WO03/074993

PCT Pub. Date: Sep. 12, 2003

(65) Prior Publication Data

US 2004/0233433 A1 Nov. 25, 2004

(30) Foreign Application Priority Data

Mar. 6, 2002 (JP) .............................. 2002-059915

(51) Int. Cl.
*G01J 4/00* (2006.01)
(52) U.S. Cl. ...................................... 356/364; 356/369
(58) Field of Classification Search ................ 356/364, 356/369, 370, 36, 445, 244
See application file for complete search history.

(56) References Cited

U.S. PATENT DOCUMENTS

| 5,457,535 A | 10/1995 | Schmidtke et al. |
| 5,856,873 A | 1/1999 | Naya et al. |
| 5,926,284 A * | 7/1999 | Naya et al. .................. 356/445 |

FOREIGN PATENT DOCUMENTS

CN 87 1 02016 A 11/1988

(Continued)

OTHER PUBLICATIONS

Chinese Office Action for 038007002, dated Mar. 18, 2005, with partial English language translation.

(Continued)

*Primary Examiner*—Layla G. Lauchman
*Assistant Examiner*—Roy M. Punnoose
(74) *Attorney, Agent, or Firm*—RatnerPrestia (57) ABSTRACT

To provide a concentration measuring method which enables a stable and highly accurate concentration measurement while avoiding the step of making a background measurement.

The concentration measuring apparatus includes: a concentration measuring contact that is brought into contact with a subject of measurement; a light source that emits light and enters the light into the concentration measuring contact; a polarizer that takes out p-polarized and s-polarized light components from the light which is passed through the concentration measuring contact into the subject of measurement, transmitted in the subject of measurement, and returned to the concentration measuring contact; a photodetector that determines at least the quantities of the p-polarized and s-polarized light components taken out by the polarizer; and calculating means that calculates the concentration of a specific component contained in the subject of measurement based on the determined results.

10 Claims, 7 Drawing Sheets

FOREIGN PATENT DOCUMENTS

| | | |
|---|---|---|
| JP | 05-203566 A | 8/1993 |
| JP | 09-113439 | 5/1997 |
| JP | 09-325113 A | 12/1997 |
| JP | 10-038694 A | 2/1998 |
| JP | 11-101739 A | 4/1999 |
| WO | WO 03/021239 A1 | 3/2003 |

OTHER PUBLICATIONS

Japanese International Search Report for PCT/JP03/02534, dated Jul. 8, 2003.

D. Bach et al., "Attenuated total reflection (ATR) Fourier transform infrared spectroscopy of dimyristoyl phosphatidylserine-cholesterol mixtures", Biochimica et Biophysica Acta, vol. 1514, No. 2, (2001), pp. 318-326.

M. Larsson et al., "Structure and Orientation of Collectors Adsorbed at the ZnS/Water Interface", Journal of Colloid and Interface Science, vol. 242, No. 1, (2001), pp. 25-30.

B. Jordanov et al., "An ATR Method for Measurement of IR Circular Dichroic Spectra", Journal of Molecular Structure, vol. 141 (Mar. 1986) pp. 297-300.

K. Kurihara et al., "Hydrogen-bonded Macrocluster Formation of Ethylene Glycol on Silica Surfaces in Ethylene Glycol-Cyclohexane Binary Liquids", Chemistry Letters, vol. 32, No. 1 (2003), pp. 84-85.

H. Fukushima et al., "Diabetes and BME, Noninvasive Blood Glucose Measurement, Development of Optical Glucose Sensor", BME, vol. 5, No. 8, (Japan ME Society, 1991).

* cited by examiner

CONCENTRATION MEASURING INSTRUMENT, CONCENTRATION MEASURING CONTACT APPARATUS, CONCENTRATION MEASURING CALCULATING APPARATUS, AND CONCENTRATION MEASURING METHOD

This application is a U.S. national phase application of PCT isternational application PCT/JP03/02534.

TECHNICAL FIELD

The present invention relates to a concentration measuring instrument, concentration measuring contact apparatus, concentration measuring calculating apparatus, and concentration measuring method of measuring concentrations of glucose, cholesterol, ethanol, etc.

BACKGROUND ART

A variety of methods have been proposed which measure specific components in specimens, particularly in living bodies and solutions using an attenuated total reflectance (hereinafter referred to as ATR) measuring instrument.

Figure 7:
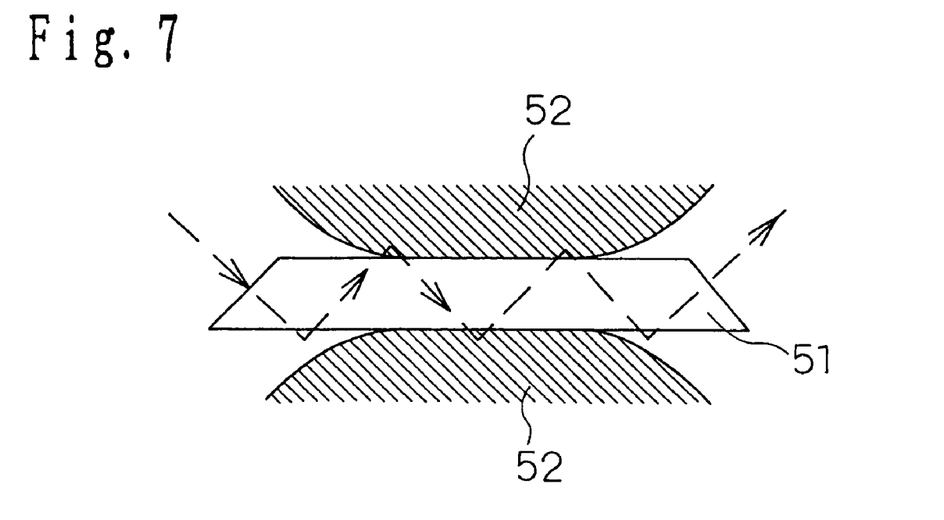
FIG. 7 is a schematic diagram showing a concentration measuring method which uses the conventional ATR device.

For example, in Japanese Patent Laid-Open No. 9-113439, there is proposed a method of measuring the blood sugar level using a transparent ATR device 51 having a pair of parallel reflecting surfaces opposing each other in which measurement is made with upper and lower lips 52, as a specimen, brought into tight contact with the ATR device 51, as shown in FIG. 7. According to this method, the measurement of the blood sugar level is made through the following procedures: inserting an ATR device 51 between upper and lower lips, and getting the same to be hold firmly by the lips; entering light into the ATR device 51 so that the light is allowed to undergo total reflection repeatedly at the interface between each reflection surface of the ATR device 51 and the lips 52, as shown by the broken line in FIG. 7; and analyzing the light that oozes out of the ATR device 51. The entire disclosure of Japanese Patent Laid-Open No. 9-113439 is incorporated herein by reference in its entirety.

In BME, Vol. 5, No. 8 (Japan ME Society, 1991), there is proposed a method which measures the blood sugar level, the concentration of ethanol in blood, etc. using an ATR device made up of ZnSe optical crystal etc. In the method, measurements are made through the following procedures: bringing the ATR device into tight contact with lip mucosa; entering a laser light with a wavelength of 9 to 11 microns into the ATR device and allowing the light to undergo multiple reflection inside the ATR device; and analyze the absorbed and scattered light. The entire disclosure of BME, Vol. 5, No. 8 (Japan ME Society, 1991) is incorporated herein by reference in its entirety.

According to this method, concentrations of specific components such as glucose, ethanol and cholesterol can be measured non-invasively and in real time. This method is to apply evanescent light (known as ooze-out light) to a quantitative analysis. Only a very small quantity of the light traveling in the ATR device actually enters lips, and the light having entered the lips is affected by components in the body fluid existing in the lips.

For example, in glucose, its light absorption peaks at a wave number of 1080 cm$^{-1}$; therefore, when applying light with the above wave number to a living body, the quantity of the light absorption of glucose changes depending on the glucose concentration in the living body. Accordingly, if the quantity of the light returned from the living body is measured, the change in quantity of the light absorption of a component in body fluid with change in the concentration of the component can be detected, in other words, the concentration of the component can be obtained.

Figure 8:
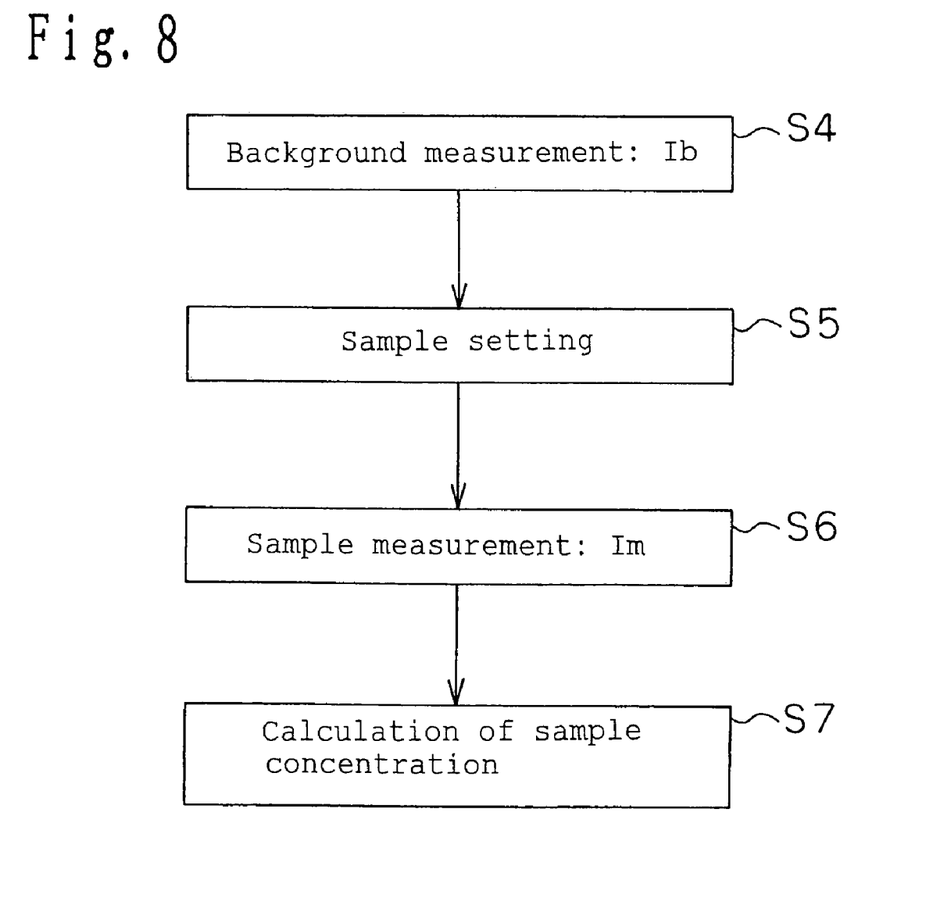
FIG. 8 is a flow diagram showing a measurement flow of the conventional concentration measuring method.

When measuring the absorbance of a substance surface with an ATR measuring instrument and calculating the concentration of the same using the measured absorbance, the measuring method shown in FIG. 8 has been commonly used.

First, in the background measuring step, the measurement of background is made by entering light emitted by a light source into the ATR device, carrying out spectrometry of a reference, such as air or deionized water, while keeping the ATR device out of contact with a sample as a subject of measurement, and storing the measured results in a memory (S4). The reasons for the background measurement are to correct the wavelength characteristics of a light source and a photodetector and to ensure an accurate absorbance measurement or concentration calculation even after their characteristics have changed with time.

Then, the sample as a subject of measurement is set so that it comes in contact with the ATR device (S5) and measurement is made for the sample (S6).

Calculation is carried out according to the following equation, $\text{Log}_{10}$ (Ib/Im), where Ib represents a detected signal from the photodetector at the time of background measurement and Im a detected signal from the photodetector at the time of measurement for the sample (S7). The calculated value is commonly referred to as absorbance. Since absorbance correlates with concentration of a specific components in a sample, if a calibration curve of absorbance and concentration is prepared in advance, the concentration of a specific component in the sample can be estimated from the calculated absorbance.

The conventional ATR measuring instruments described above, however, have the following problems.

When making measurement of a sample after a certain length of time has elapsed since the completion of background measurement, the intensity of the light source and the sensitivity of the photodetector have changed delicately, which has made accurate measurement of the sample difficult.

Further, when measuring the spectral characteristics of a sample, in order to make the measurement accurate, it is necessary to set the contact position and the contact area, where the sample and the ATR device are in contact with each other, just the same as those at the time of background measurement. However, such setting has been difficult to perform accurately; as a result, the obtained accuracy of measurement has not been satisfactory. Particularly when the sample has been a living body, it has been difficult to accurately position the sample and the ATR device at the time of measurement.

DISCLOSURE OF THE INVENTION

The present invention has been made in the light of the above described problem. Accordingly, the object of the invention is to provide a concentration measuring apparatus, concentration measuring contact apparatus, concentration measuring calculating apparatus, and concentration measuring method which enables stable and highly accurate concentration measurement while avoiding the step of making background measurement.

To solve the above problems, a first aspect of the present invention is a concentration measuring apparatus, comprising:

a concentration measuring contact (2) that is brought into contact with a subject of measurement;

a light source that emits light and enters the light into the concentration measuring contact;

a polarizer that takes out p-polarized and s-polarized light components from the light which is passed through the concentration measuring contact into the subject of measurement, transmitted in the subject of measurement, and returned to the concentration measuring contact;

a photodetector that determines at least the quantities of the p-polarized and s-polarized light components taken out by the photodetector; and calculating means that calculates the concentration of a specific component contained in the subject of measurement based on the determined results.

A second aspect of the present invention is the concentration measuring apparatus according to the first aspect of the present invention, wherein the calculating means calculates the concentration of the specific component utilizing correspondence information obtained in advance that allows the determined results to have a one-to-one correspondence with the concentrations of the specific component.

A third aspect of the present invention is the concentration measuring apparatus according to the first aspect of the present invention, wherein the concentration measuring contact is an attenuated total reflection device and the light entered into the subject of measurement is evanescent light that oozes from the attenuated total reflection device.

A fourth aspect of the present invention is the concentration measuring apparatus according to the first aspect of the present invention, wherein the subject of measurement is a living body tissue and the specific component is glucose, ethanol, cholesterol or a derivative of cholesterol.

A fifth aspect of the present invention is the concentration measuring apparatus according to the first aspect of the present invention, wherein the calculating means carries out calculation according to the equation, log10 (Is/Ip) or log10 (Ip/Is), where Ip represents the measured value of the quantity of the p-polarized light component and Is represents the measured value of the quantity of the s-polarized light component, and obtains the concentration of the specific component based on the calculated value.

A sixth aspect of the present invention is the concentration measuring apparatus according to the first aspect of the present invention, wherein the calculating means carries out calculation according to the equation, Ip/Is or Is/Ip, where Ip represents the measured value of the quantity of the p-polarized light component and Is represents the measured value of the quantity of the s-polarized light component and obtains the concentration of the specific component based on the calculated value.

A seventh aspect of the present invention is the concentration measuring apparatus according to the first aspect of the present invention, wherein the photodetector measures the quantities of the p-polarized light component and the s-polarized light component alternately at least one time or more for each, the calculating means (8) selects, from among the measured values measured by the photo detector, the measured value of Ip, the quantity of the p-polarized light component, and the measured value of Is, the quantity of the s-polarized light component, the values being obtained at the respective measurement time points in immediate proximity to each other, carries out calculation using the selected Ip and Is values, and obtains the concentration of the specific component based on the calculated value.

The eighth aspect of the present invention is also a concentration measuring method of measuring a specific component contained in a subject of measurement including:

a contacting step of bringing the concentration measuring contact into contact with the subject of measurement;

a light entering step of entering light into the concentration measuring contact;

a measuring step of measuring at least the quantities of the p-polarized light component and the s-polarized light component of the light that is passed through the concentration measuring contact into the subject of measurement, transmitted in the subject of the measurement, and returned to the concentration measuring contact; and a calculating step of calculating the concentration of the specific component contained in the subject of measurement based on the determined results in the measuring step.

The ninth aspect of the present invention is also a concentration measuring contact apparatus including:

a concentration measuring contact (2) that is brought into contact with a subject of measurement;

a light source (1) that emits light and enters the light into the concentration measuring contact (2);

a polarizer (7) that takes out p-polarized and s-polarized light components of the light that is passed through the concentration measuring contact (2) into the subject of measurement, transmitted in the subject of measurement, and returned to the concentration measuring contact (2); and a photodetector (6) that determines at least the quantities of the p-polarized light component and the s-polarized light component taken out by the polarizer, wherein the concentration of a specific component contained in the subject of measurement is calculated by calculating means based on the determined results.

The tenth aspect of the present invention is also a concentration measuring calculating apparatus including:

calculating means (8) that calculates the concentration of a specific component contained in a subject of measurement based on determined results obtained by a concentration measuring contact apparatus which includes:

a concentration measuring contact (2) that is brought into contact with the subject of measurement;

a light source (1) that emits light and enters the light into the concentration measuring contact (2);

a polarizer (7) that takes out p-polarized and s-polarized light components of the light that is passed through the concentration measuring contact (2) into the subject of measurement, transmitted in the subject of measurement, and returned to the concentration measuring contact (2); and a photodetector (6) that determines at least the quantities of the p-polarized light component and the s-polarlized light component taken out by the polarizer. The present invention may be the third invention.

DESCRIPTION OF SYMBOLS

1 Light Source
2 Concentration Measuring Contact
3 Light Input Portion
4 Contact Portion
5 Light Output Portion
6 Photodetector
7 Polarizer
51 ATR device
52 Lips Best Mode for Carrying Out the Invention In the following, embodiments of the present invention will be described with reference to the accompanying drawings.

Figure 1:
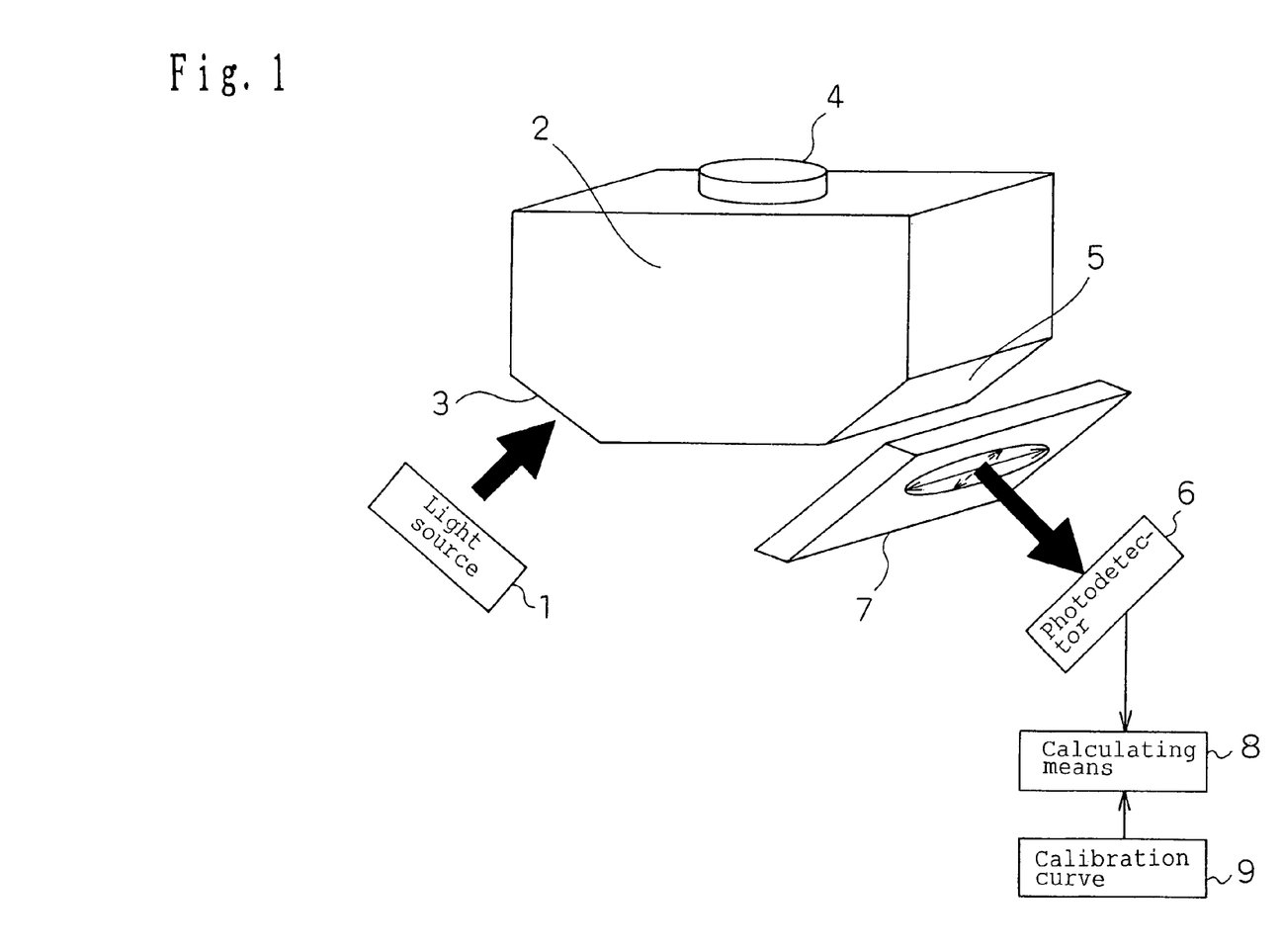
FIG. 1 is a schematic diagram of a concentration measuring contact which is used in a concentration measuring method of measuring a specific component contained in a subject of measurement in accordance with one embodiment of this invention.

FIG. 1 is a schematic diagram of a concentration measuring contact which is used in a method of measuring the concentration of concentrations of specific components in subjects of measurement in accordance with one embodiment of the invention.

With this embodiment, one case will be described in which a concentration of glucose, as a specific component in a subject of measurement, is measured.

As a light source 1, a light source that emits mid-infrared light is used. In this embodiment, a SiC light source is used as the light source 1. The SiC light source is particularly suitable for making concentration measurements for substances whose absorption wave number is in the fingerprint region (mid-infrared region) of, for example, 1080 cm$^{-1}$ and 1033 cm$^{-1}$.

As a material for a concentration measuring contact 2, is preferably used a material which is capable of transmitting mid-infrared light, chemically stable and excellent in mechanical strength. In this embodiment, germanium is used as the material for the concentration measuring contact 2.

A contact portion 4 is brought into contact with a subject of measurement. For example, when measuring the concentration of a glucose solution, the glucose solution is dropped onto the contact portion 4 so that the solution covers the entire surface of the contact portion 4. The glucose solution never overflows the contact portion 4, due to the effect of its surface tension, and a suitable amount of solution required for the concentration measurement is kept on the contact portion 4, which allows stable measurement of the glucose concentration in the solution.

When the subject of measurement is a living body, the living body is brought into tight contact with the contact portion 4. In this case, the area of the portion which is in tight contact with the living body is preferably 2 cm$^2$ or less. When the area is about 2 cm$^2$ or less, the contact portion eats deeper into the living body and its contact with the living body becomes much tighter, which allows stable measurements. As for the portion of the living body which is brought into tight contact with the contact portion 4, the portion whose stratum corneum is thin is preferable, specifically proximal nail wall at the base of a finger-nail, lips and oral mucosa are preferable.

Preferably the shape of the contact portion 4 is, but not limited to, approximately circular. The reason is that when the subject of measurement is a living body, the circular shape lessens the pain the subject suffers at the time of measurement. More preferably the periphery of the contact portion 4 is provided with a chamfered portion or a rounded portion, because providing such portions much lessens the pain of the subject.

As a photodetector 6, an MCT photodetector is used in this embodiment.

A polarizer 7 functions to take out a specific component of polarized light. In this embodiment, a wire grid polarizer is used in which a plurality of fine slits are provided. Rotating the polarizer 7 makes it possible to arbitrarily set the component of polarized light that reaches the photodetector 6 to s-polarized light or p-polarized light. The position of the polarizer 7 is not limited to the position shown in FIG. 1, it has only to be positioned on the optical path between the light source 1 and the photodetector 6.

In FIG. 1, the direction shown by the solid line on the polarizer 7 denotes the vibration direction of the s-polarized light component and the direction shown by the broken line the vibration direction of the p-polarized light component. The polarizer 7 transmits light in the same vibration direction alone; therefore, measurement of the p-polarized light component, after measurement of the s-polarized light component in which the component of polarized light is set to the direction shown by the solid line, needs to rotate the polarizer 7 at an angle of about 90 degrees.

Providing, for example, spectroscopic means (not shown in the figure) between the light source 1 and the concentration measuring contact 2 is preferable, because it allows the measurement of the wavelength-spectral characteristics of the specific component and obtaining the absorption characteristics of the same at different wavelengths. The spectroscopy, FT-IR method, which uses an interferometer is particularly preferable as spectroscopic means, because it allows highly sensitive measurement.

Calculating means 8 calculates the concentration of a glucose solution from the measurements obtained by the photodetector 6 utilizing correspondence information 9. As the calculating means 8, a microcomputer or a personal computer made up of a CPU and a memory is used.

The calibration curve 9 is a collection of data obtained through the following procedures: measuring in advance concentrations of glucose solutions, whose concentrations are already known, by the method of measuring the concentration of specific components in analytes in accordance with the embodiment of the present invention; and getting the measured results to have one to one correspondence to the known concentrations of glucose solutions. The calibration curve 9 is stored in, for example, the above described microcomputer or personal computer in advance.

The calibration curve 9 of this embodiment is one example of correspondence information of this invention.

Figure 2:
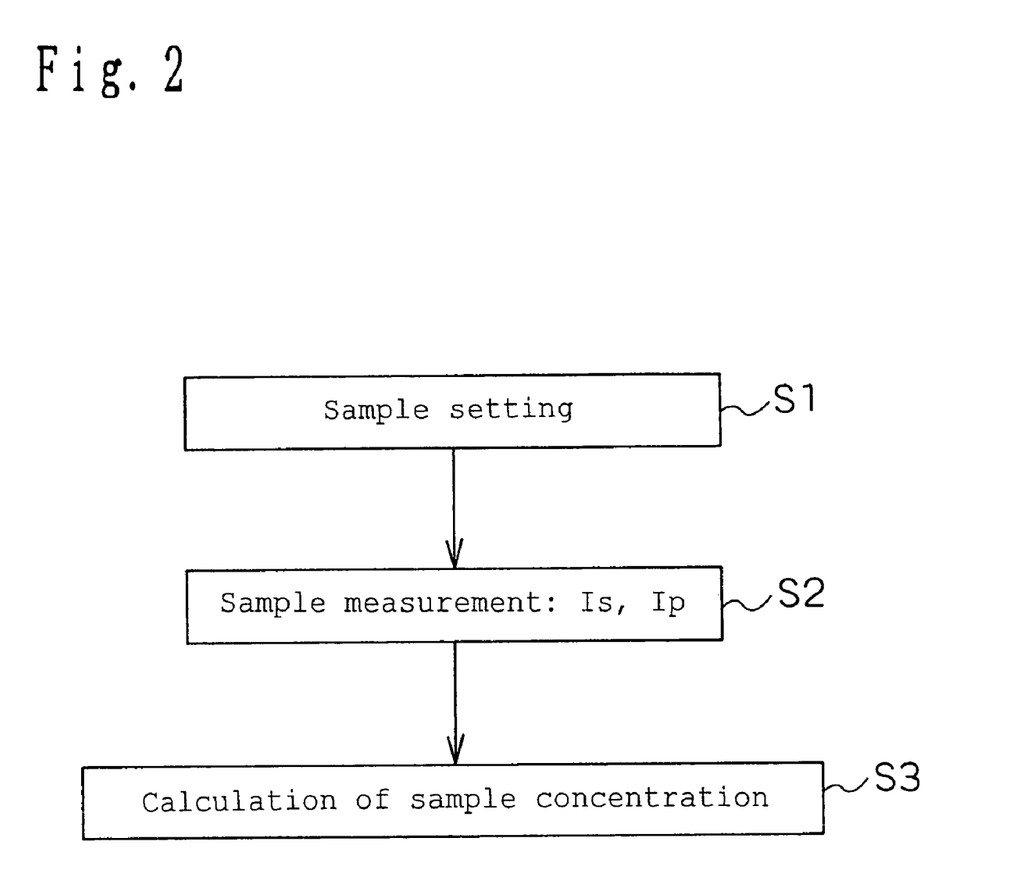
FIG. 2 is a flow diagram showing a measurement flow of the concentration measuring method of measuring a specific component in a subject of measurement in accordance with one embodiment of this invention.

Then, the measurement flow of the concentration measuring method of measuring a specific component contained in a subject of measurement in accordance with this embodiment will be described with reference to FIG. 2.

First, a glucose solution as a subject of measurement is set on the contact portion of a concentration measuring contact (S1). In this step, background measurement using air or deionized water, which has been required for the conventional concentration measuring method, is not needed. Then, spectral characteristics of the glucose solution to polarized light are measured with the glucose solution set on the contact portion (S2). As the spectral characteristics to polarized light, for example, spectral characteristics to s-polarized light and p-polarized light are measured. Then, in the calculating means 8, calculation is carried out using the measured value of the polarized light components and the concentration of glucose in the glucose solution is calculated based on the obtained value (S3). As the calculation, for example, the value, Ip/Is where Is represents the measured value of the s-polarized light component and Ip the measured value of the p-polarized value component, is calculated.

Then, a concentration measuring method using the concentration measuring contact in accordance with this embodiment will be described with reference to FIG. 1.

A glucose solution, as a subject of measurement, is dropped on the surface of the contact portion 4 so that the entire contact portion 4 is filled with the solution. Light emitted by the light source 1 is entered into the contact portion 4 at an incident angle of θ so that it undergoes total reflection. At this time, evanescent light is oozed from the contact portion 4, transmitted in the glucose solution, returned to the contact portion 4, passed through a light output portion 5 to its outside, and allowed to reach the photodetector 6 through the polarizer 7.

The spectral characteristics of the glucose solution to the s-polarized light component is measured while setting the polarizer 7 in such a manner as to allow the light having a plane of vibration in the direction shown by the solid line in the figure, that is, the s-polarized light to pass through the polarizer 7. Then the polarizer 7 is rotated at an angle of 90 degrees and the spectral characteristics of the glucose solution to the p-polarized light component are measured. The measurement is completed at this point. The value, Ip/Is, is calculated using the measured values Ip, Is at the respective wave numbers and the concentration of glucose is calculated using the above values and the calibration curve 9 obtained in advance.

In this measurement, it is preferable to set the incident angle θ of the light entered into the contact portion 4 so that the value, z/λ, calculated using the following equation (1) becomes 0.25 or more.

$$\frac{z}{\lambda} = \frac{1}{2\pi\sqrt{nf^2\sin^2\theta - nc^2}}$$ (Mathematical Equation 1)

wherein z represents the depth (unit: micron) to which the light entered into the contact portion oozes out of it, λ the wavelength (unit: micron) of the light entered into the contact portion, nf the refractive index of the contact portion, θ the incident angle of the light entered into the contact portion, and nc the refractive index of the subject of measurement.

For example, in cases where the refractive index nc of the glucose solution, as the subject of measurement, for the light with a wavelength of about 9.6 microns is 1.24, if germanium, whose refractive index nf is 4, is used for the contact portion, the incident light θ which satisfies z/λ=0.25 is about 45 degrees. If light is entered into the contact portion at such an incident angle, the absorbance of the subject of measurement differed largely depending on whether the incident light is the s-polarized light or the p-polarized light. The concentration of a specific component can be detected by the difference in absorbance created depending on whether the incident light is the s-polarized light or the p-polarized light. Specifically, the s-polarized light oozes into the subject of measurement only to a shallower portion, whereas the p-polarized light oozes into the subject of measurement to a deeper portion. And the s-polarized light is hardly affected by the concentration of the specific component contained in the subject of measurement. In other words, the measurement of the quantity of the s-polarized light corresponds to the measurement of background in the prior art and the measurement of the quantity of the p-polarized light corresponds to the measurement for the sample in the prior art. Thus, the concentration of the specific component can be detected by measuring the quantities of the s-polarized light and the p-polarized light.

This method is effective when the incident angle of the light entered into the contact portion is about 45 degrees or less, but preferably the incident angle is larger than critical angle. If the incident angle is smaller than critical angle, the light does not satisfy the total reflection requirements; as a result, the light is scattered in the subject of measurement, which decreases the quantity of light returned to the contact portion, and in addition, the optical path difference between the p-polarized light and the s-polarized light is decreased. Experiments showed that when z/λ=0.9 or more, in other words, when using germanium for the contact portion and setting the incident angle to 21 degrees or 20 degrees, particularly satisfactory results were obtained, and when setting the incident angle to 19 degrees, much more satisfactory results were obtained.

Generally, when making measurement using an FT-IR spectroscope, in many cases measuring operation is repeated several times while scanning the wavelength and the average measured value is calculated. This invention is also effective in such a measuring method. For example, it is preferable to make measurement for each polarized light component several times and then calculate the average measured value.

The operations of measuring an s-polarized light component and measuring a p-polarized light component may be carried out alternately. In such a case, it is preferable to calculate Ip/Is, Is/Ip, $\log_{10}$ (Ip/Is) or $\log_{10}$ (Is/Ip) based on the measured results of the s-polarized and p-polarized light components which are obtained at the respective measuring times in immediate proximity to each other, because to do so makes it possible to prevent to the utmost the measured results from being affected by the change in the light source and the photodetector with time.

It should be noted that this embodiment has been described taking the case where a SiC light source is used as the light source 1, but the light source is not limited to this. For example, tungsten is preferably used as the light source 1. A quantum cascade laser is more preferably used as the light source 1. These light sources are particularly suitable for measuring the concentrations of substances, such as glucose, whose absorption wave numbers are in the fingerprint region (mid-infrared region) of about 1080 cm$^{-1}$ to 1033 cm$^{-1}$, like the case where a SiC light source is used.

Further, this embodiment has been described taking the case where germanium is used as the material for the concentration measuring contact 2, but the material for the concentration measuring contact 2 is not limited to this. Silicon, which is capable of transmitting mid-infrared light, chemically stable and excellent in mechanical strength, can also be used as the material for the concentration measuring contact 2.

When using silicon as the material for the concentration measuring contact 2, a silicon single crystal substrate is used which is transparent to light with a wavelength of 1.1 to 10 microns. Silicon having small content of impurities, such as boron and phosphorus, and having resistivity of 100 Ωcm or more is particularly preferable. Silicon having resistivity of 1500 Ωcm or more is much more preferable. The silicon having such high resistivity has high transmissivity at infrared wavelength of about 9 to 10 microns, and it is preferably used when measuring the concentration of substances, such as glucose, whose absorption region is in this wavelength band.

Preferably an antireflection film is provided on the surface of the light input portion 3. As a material for the antireflection film, diamond-like carbon (DLC) or ZnSe is used. The thickness of the antireflection film is preferably 1.1 to 1.3 microns, more preferably about 1.2 microns.

Preferably an antireflection film is provided on the surface of the light output portion 5, like the light input portion 3.

Further, this embodiment has been described taking the case where an MCT photodetector is used as the photodetector 6, but the photodetector is not limited to this. A pyroelectric sensor may also be used as the photodetector 6.

The calibration curve 9 may be a table in which the measured results are allowed to have one to one correspondence to the known concentrations of glucose solutions or a mathematical equation by which the measured results are allowed to have one to one correspondence to the known concentrations of glucose solutions.

Further, this embodiment has been described taking a case where a wire grid polarizer is used as the polarizer 7, but the polarizer is not limited to this. As the polarizer 7, an interference filter type of polarizer can also be used which transmits a p-polarized light component and reflects an s-polarized light component.

Figure 6:
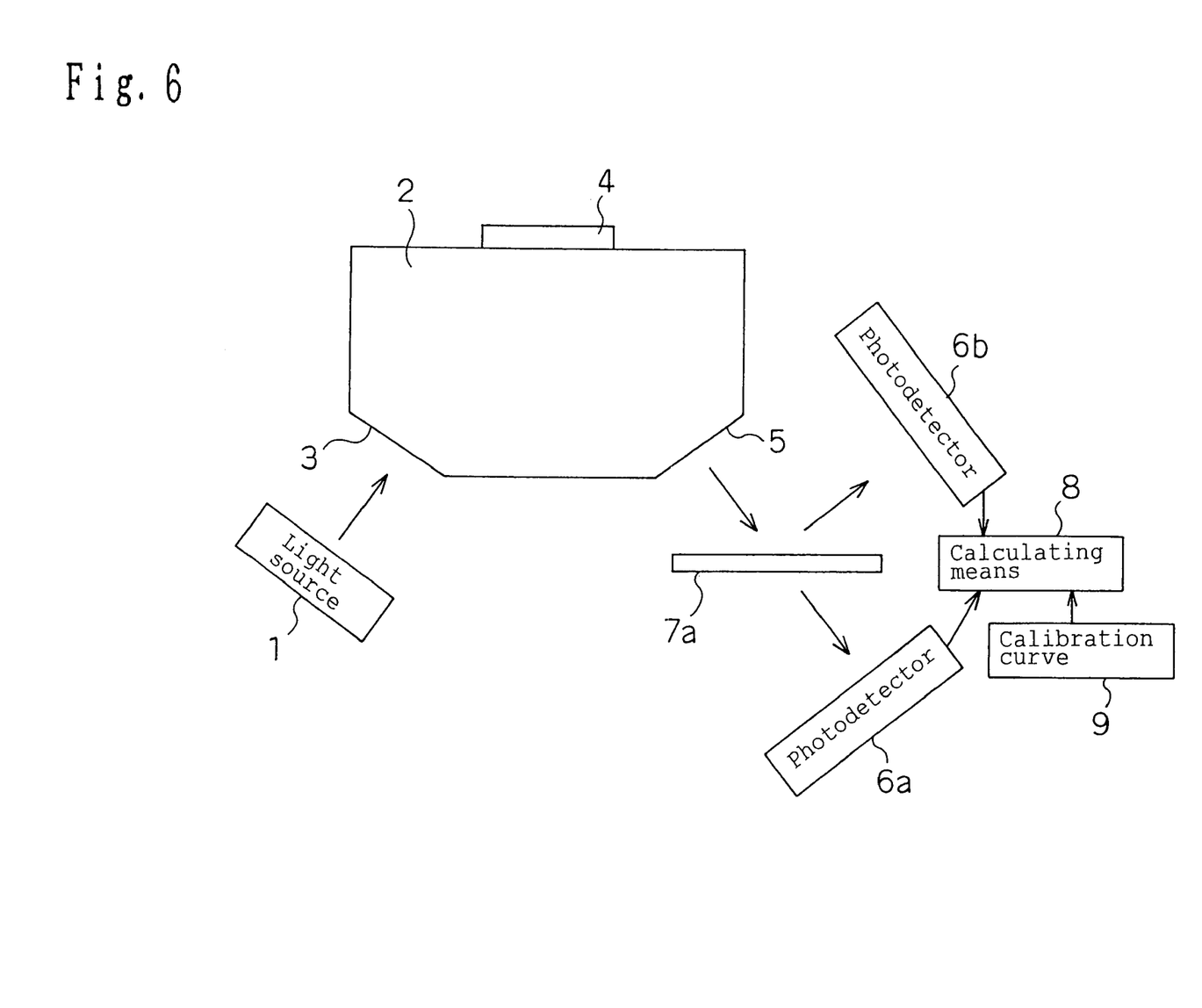
FIG. 6 is a schematic diagram of a concentration measuring contact which is used in a concentration measuring method of measuring a specific component contained in a subject of measurement in accordance with the same embodiment of this invention, in which an interference filter type of polarizer is used as a polarizer.

FIG. 6 is a schematic diagram of a concentration measuring contact which uses a polarizer 7a, as an interference filter type of polarizer, instead of the polarizer 7 and is used in a concentration measuring method of measuring a specific component in a subject of measurement. In FIG. 6, the same parts as those of FIG. 1 are denoted by the same reference numerals and detailed description thereof will be omitted.

The polarizer 7a functions to take out specific polarized light components just like the polarizer 7 of FIG. 1. The difference between the polarizer 7a and the polarizer 7 is in that the polarizer 7a reflects an s-polarized light component and transmits a p-polarized light component, as described above.

Accordingly, in FIG. 6, unlike FIG. 1, a photodetector 6a of detecting the quantity of a p-polarized light component, that is, light transmitted in the polarizer 7a and a photodetector 6b of detecting the quantity of an s-polarized light component light, that is, light reflected by the polarizer 7a are arranged. As the photodetector 6a, 6b, pyroelectric sensors are used. As the photodetector 6a, 6b, MCT photodetectors may also be used.

With the concentration measuring contact shown in FIG. 6, since s-polarized and p-polarized light components can be measured by the photodetectors 6a, 6b at the same time, it is not necessary to measure the spectral characteristics through the two-step procedure of: measuring the spectral characteristic of a glucose solution to s-polarized light component while setting the polarizer 7 so that it transmits the s-polarized light component and then the polarizer 7 is rotated at an angle of 90 degrees, and measuring the spectral characteristic to p-polarized light component while keeping the polarizer 7 in such a state. Accordingly, this embodiment gives effect of being less affected by the change of the light source 1.

Further, this embodiment has been described taking the case where a glucose solution is used as a subject of measurement, the subject of measurement is not limited to this. The concentration measuring contact in accordance with this embodiment is useful for measuring the concentration of glucose not only in a glucose solution, as a subject of measurement, but also in blood plasma and in a living body. When the specific component in a subject of measurement is a component other than glucose, such as cholesterol, ethanol or the derivative of cholesterol, this embodiment can be effectively applied. However, the specific component in a subject of measurement is changed, the wavelength of light to be measured is also changed.

Specifically, when the specific component of a subject of measurement is cholesterol or the derivative of cholesterol, since the absorption wavelength of cholesterol is 1500 nm or 1700 nm, a light source that emits light with such a wavelength should be used as a light source 1 or a photodetector that detects light with such a wavelength should be used. When the specific component of a subject of measurement is ethanol, since the absorption wave number of ethanol is 1240 cm$^{-1}$ or 1400 cm$^{-1}$, a light source that emits light with such a wave number should be used as a light source or a photodetector that detects light with such a wave number should be used. When the specific component of a subject of measurement is different from the above described ones, if a light source that emits light with an absorption wave numbers of the specific component of the subject of measurement is used or a photodetector that detects light with such a wave number is used, the concentration of the specific component in the subject of measurement can be measured, like the above described components.

As described above, according to this embodiment, a concentration measuring method of measuring specific component in a subject of measurement is provided which enables stable and highly accurate concentration measurement while avoiding the step of carrying out background measurement. The concentration measuring method of measuring a specific component of this invention is useful for measuring the concentration of glucose not only in a glucose solution, but also in blood plasma, in a living body, etc.

EXAMPLE

Figure 3:
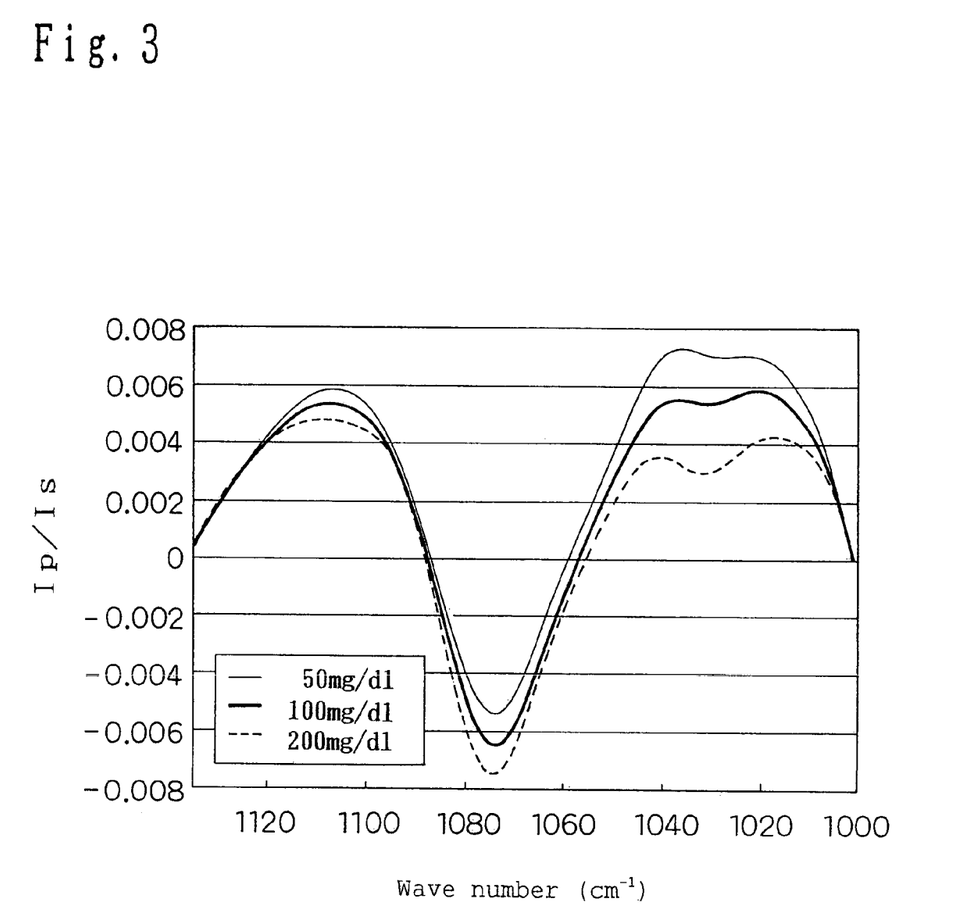
FIG. 3 illustrates characteristic curves showing incident light wave number dependency of the value, Ip/Is, obtained by the concentration measuring method of measuring a specific component in a subject of measurement in accordance with the same embodiment of this invention.

The concentration of glucose in a glucose solution was measured using a concentration measuring contact shown in FIG. 1. FIG. 3 illustrates characteristic curves showing incident light wave number dependency of the values, Ip/Is, which were obtained by making measurement for glucose solutions with different concentrations. In the measurement, glucose solutions with different concentrations, 50, 100 and 200 mg/dl, were used. And baseline correction was made so that the values, Ip/Is, become zero at wave numbers of 1135 cm$^{-1}$ and 1000 cm$^{-1}$.

For example, when giving attention to the wave numbers 1076 cm and 1033 cm$^{-1}$, it is seen that with the increase of the glucose concentration, the values, Ip/Is, are decreased and there is correlation between the glucose concentration and the value, Ip/Is.

Figure 4:
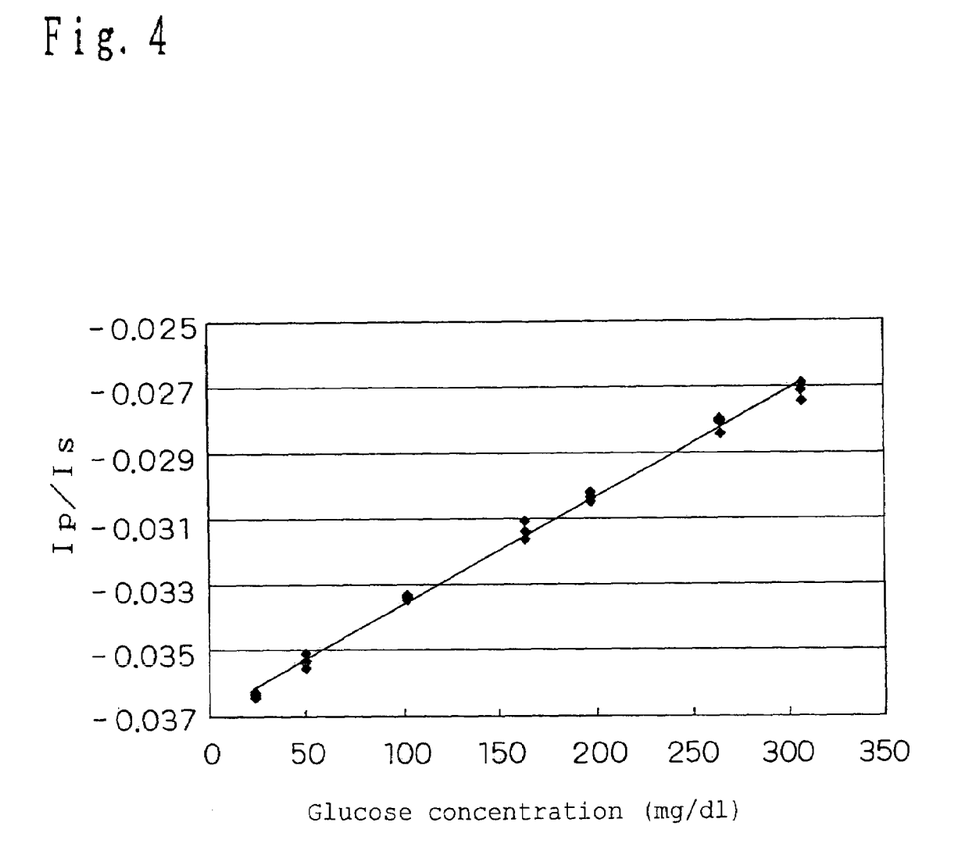
FIG. 4 is a graph showing the relation between the value, Ip/Is, and the glucose concentration obtained by the concentration measuring method of measuring a specific component in a subject of measurement in accordance with the same embodiment of this invention.

FIG. 4 shows the relation between the values, Ip/Is, and the glucose concentration at a wavelength of 1033 cm$^{-1}$. It is seen from the figure that there is straight line relationship and satisfactory correlation between the values, Ip/Is, and the glucose concentration. Thus, even when background measurement, which is a step included in the conventional concentration measuring method, was not carried out, the glucose concentration could be calculated easily only by obtaining the value, Ip/Is, using the measured values Ip and Is. And the relation between the values, Ip/Is, and the glucose concentration shown in FIG. 4 can be used as a calibration curve 9, which should obtained in advance.

Figure 5:
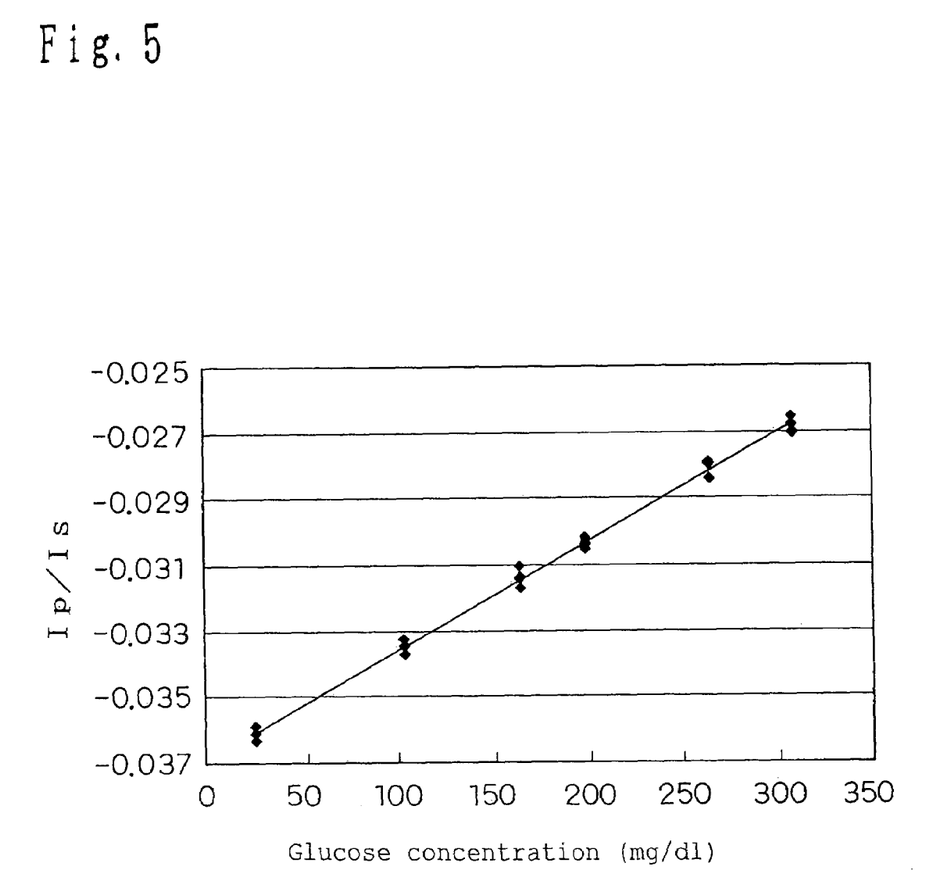
FIG. 5 is a graph showing the relation between the value, Ip/Is, and the glucose concentration in accordance with the same embodiment of this invention which are obtained using a light source whose quantity of light is decreased by 10% compared with that of the light source with which the relation between the value, Ip/Is, and the glucose concentration shown in FIG. 4 is obtained.

FIG. 5 shows the relation between the values, Ip/Is, and the glucose concentration which are obtained using a light source whose quantity of light is decreased by 10% compared with that of the light source with which the relation between the value, Ip/Is, and the glucose concentration shown in FIG. 4 is obtained. Comparing FIG. 4 with FIG. 5, it is seen that the Ip/Is—glucose concentration relations of both cases are substantially the same straight line. Thus, it is apparent that obtaining the value, Ip/Is, like in this embodiment, makes it possible to obtain glucose concentration with a high accuracy, even when the quantity of light from the light source is decreased due to its change with time This embodiment has been described taking the case where glucose concentration is obtained using the value, Ip/Is, the value used is not limited to this. The same effect can be obtained when using the value, Is/Ip, log$_{10}$ (Ip/Is) or log$_{10}$ (Is/Ip).

INDUSTRIAL APPLICABILITY

As is apparent from the description so far, according to this invention, a concentration measuring apparatus, concentration measuring contact apparatus, concentration measuring calculating apparatus, and concentration measuring method can be provided which enables stable and highly accurate concentration measurement while avoiding the step of carrying out background measurement.

The invention claimed is:

1. A concentration measuring apparatus, comprising:
    a concentration measuring contact that is brought into contact with a subject of measurement;
    a light source that emits light and enters the light into the concentration measuring contact;
    a polarizer that takes out p-polarized and s-polarized light components from the light which is passed through the concentration measuring contact into the subject of measurement, transmitted in the subject of measurement, and returned to the concentration measuring contact;
    a photodetector that determines at least the quantities of the p-polarized and s-polarized light components taken out by the photodetector; and
    calculating means that calculates the concentration of a specific component contained in the subject of measurement based on the determined results.

2. The concentration measuring apparatus according to claim 1, wherein the calculating means calculates the concentration of the specific component utilizing correspondence information obtained in advance that allows the determined results to have a one-to-one correspondence with the concentrations of the specific component.

3. The concentration measuring apparatus according to claim 1, wherein the concentration measuring contact is an attenuated total reflection device and the light entered into the subject of measurement is evanescent light that oozes from the attenuated total reflection device.

4. The concentration measuring apparatus according to claim 1, wherein the subject of measurement is a living body tissue and the specific component is glucose, ethanol, cholesterol or a derivative of cholesterol.

5. The concentration measuring apparatus according to claim 1, wherein the calculating means carries out calculation according to the equation, log10 (Is/Ip) or log10 (Ip/Is), where Ip represents the measured value of the quantity of the p-polarized light component and Is represents the measured value of the quantity of the s-polarized light component, and obtains the concentration of the specific component based on the calculated value.

6. The concentration measuring apparatus according to claim 1, wherein the calculating means carries out calculation according to the equation, Ip/Is or Is/Ip, where Ip represents the measured value of the quantity of the p-polarized light component and Is represents the measured value of the quantity of the s-polarized light component and obtains the concentration of the specific component based on the calculated value.

7. The concentration measuring apparatus according to claim 1, wherein the photodetector measures the quantities of the p-polarized light component and the s-polarized light component alternately at least one time or more for each,
    the calculating means selects, from among the measured values measured by the photo detector, the measured value of Ip, the quantity of the p-polarized light component, and the measured value of Is, the quantity of the s-polarized light component, the values being obtained at the respective measurement time points in immediate proximity to each other, carries out calculation using the selected Ip and Is values, and obtains the concentration of the specific component based on the calculated value.

8. A concentration measuring method of measuring a specific component contained in a subject of measurement comprising:
    a contacting step of bringing the concentration measuring contact into contact with the subject of measurement;
    a light entering step of entering light into the concentration measuring contact;
    a measuring step of measuring at least the quantities of the p-polarized light component and the s-polarized light component of the light that is passed through the concentration measuring contact into the subject of measurement, transmitted in the subject of the measurement, and returned to the concentration measuring contact; and
    a calculating step of calculating the concentration of the specific component contained in the subject of measurement based on the determined results in the measuring step.

9. A concentration measuring contact apparatus including:
    a concentration measuring contact that is brought into contact with a subject of measurement;

a light source that emits light and enters the light into the concentration measuring contact;

a polarizer that takes out p-polarized and s-polarized light components of the light that is passed through the concentration measuring contact into the subject of measurement, transmitted in the subject of measurement, and returned to the concentration measuring contact; and a photodetector that determines at least the quantities of the p-polarized light component and the s-polarized light component taken out by the polarizer, wherein the concentration of a specific component contained in the subject of measurement is calculated by calculating means based on the determined results.

10. A concentration measuring calculating apparatus including:

calculating means that calculates the concentration of a specific component contained in a subject of measurement based on determined results obtained by a concentration measuring contact apparatus which includes:

a concentration measuring contact that is brought into contact with the subject of measurement;

a light source that emits light and enters the light into the concentration measuring contact;

a polarizer that takes out p-polarized and s-polarized light components of the light that is passed through the concentration measuring contact into the subject of measurement, transmitted in the subject of measurement, and returned to the concentration measuring contact; and a photodetector that determines at least the quantities of the p-polarized light component and the s-polarized light component taken out by the polarizer.

* * * * *